(12) United States Patent
Burdet et al.

(10) Patent No.: US 7,326,797 B2
(45) Date of Patent: Feb. 5, 2008

(54) MANUFACTURE OF ISOFLAVONES

(75) Inventors: Bruno Burdet, Baldersheim (FR); August Ruettimann, Arlesheim (CH)

(73) Assignee: DSM IP Assets B.V., Heerlen (NL)

( * ) Notice: Subject to any disclaimer, the term of this patent is extended or adjusted under 35 U.S.C. 154(b) by 538 days.

(21) Appl. No.: 10/521,972

(22) PCT Filed: Jul. 14, 2003

(86) PCT No.: PCT/EP03/07575

§ 371 (c)(1),
(2), (4) Date: Jan. 21, 2005

(87) PCT Pub. No.: WO2004/009576

PCT Pub. Date: Jan. 29, 2004

(65) Prior Publication Data

US 2005/0256321 A1 Nov. 17, 2005

(30) Foreign Application Priority Data

Jul. 23, 2002 (EP) .................................. 02016494

(51) Int. Cl.
*C07D 311/04* (2006.01)
(52) U.S. Cl. ..................... 549/403; 549/356; 549/381; 549/396; 549/401
(58) Field of Classification Search ................ 549/200, 549/356, 381, 396, 398, 399, 401, 403
See application file for complete search history.

(56) References Cited

U.S. PATENT DOCUMENTS 7,109,358 B2 * 9/2006 Burdick ....................... 549/403

FOREIGN PATENT DOCUMENTS

WO    WO 02/085881 A1    10/2002

OTHER PUBLICATIONS

Pivovarenko and Khilya, "Mixed Anhydride of Acetic and Formic Acids in the Synthesis of Chromones. 2. Synthesis of 3-Arylchromones," *XP002211266* & *Chem. Heterocycl. Compd. (Engl. Transl.)*, vol. 28, No. 5, pp. 497-502 (1992).
Pivovarenko, V.G. et al., "Effective Synthesis of 7-Hydroxyisoflavone O-Glucosides,"*XP002211268* & *Chem. Nat. Compd. (Engl. Transl.)*, vol. 24, No. 4, pp. 432-438 (1988).
Chang, Yu-Chen et al., "Microwave-Mediated Synthesis of Anticarcinogenic Isoflavones from Soybeans,"*J. Agric. Food Chem.*, vol. 42, pp. 1869-1871 (1994).
Pivovarenko and Khilya., "Acetoformic Anhydride in the Synthesis of Chromones. 1. Synthesis of 3-Hetarylchromones,"*Chem. Heterocycl. Compound (Engl. Transl.)*, vol. 27, pp. 496-501 (1991).
Becket and Ellis, "Benzopyrones. Part XII. Novel Synthesis of Some 3-Substituted Chromones,"*Tetrahedron Letters*, No. 9, pp. 719-720 (1976).
Krishnamurty and Prasad, "A New Synthesis of Isoflavones Using 'Active Formate',"*Tetrahedron Letters*, No. 35, pp. 3071-3072 (1977).
Strazzolini, P. et al., "Acetic Formic Anhydride. A Review,"*Tetrahedron*, vol. 46, No. 4, pp. 1081-1118 (1990).
Becket, G.J.P. et al., "Benzopyrones. Part XIII. Syntheses of Some 3-Substituted Chromones,"*J. Chem. Research (S)*, p. 47 (1978).
Liu and Cheng, "A Facile and Practical Preparation of 5,7-Dihydroxy-3-(4-nitrophenyl)-4H-1-benzopyran-4-one,"*J. Heterocyclic. Chem*, vol. 28, pp. 1641-1642 (1991).

* cited by examiner

*Primary Examiner*—Golam M. M. Shameem
(74) *Attorney, Agent, or Firm*—Bryan Cave LLP

(57) ABSTRACT

A process for manufacturing a hydroxylated isoflavone of the formula (I) given in the description comprises re-acting an appropriately substituted 2-hydroxydeoxybenzoin of the formula (II), also given in the description, with a formic acid anhydride of the formula HCOOCOR3, wherein $R^3$ signifies $C_{2-20}$-alkyl or various other groups as given in the description, in presence of a base or in a solvent which acts as a base, and if necessary promoting the ensuing hydrolysis of the so-produced acylated form of the hydroxylated isoflavone of the formula I by acidification. Of particular interest as products of this process are the 5,7dihydroxyisoflavones, e.g. genistein (5,7,4'-trihydroxyisoflavone). Isoflavones display many useful biochemical effects.

16 Claims, No Drawings

MANUFACTURE OF ISOFLAVONES

This application is the National Stage of International Application No. PCT/EP2003/007575, filed Jul. 14, 2003.

The present invention concerns a process for the manufacture of certain isoflavones from appropriately substituted 2-hydroxyphenyl benzyl ketones. Of particular interest as products of this process are the 5,7-dihydroxyisoflavones, e.g. genistein (5,7,4'-trihydroxyisoflavone).

Isoflavones display many useful biochemical effects. For example, the naturally occurring and commercially available substance genistein has been claimed to be useful as an anti-inflammatory agent, for prevention and treatment of osteoporosis and heart disease, for prevention of photodamage and aging skin and wrinkles, for inhibition of Alzheimers disease and for treatment of menopausal symptoms, estrogen disorders, cancer, cataracts, cystic fibrosis and migraine. The synthetic and commercially available isoflavone irpiflavone has been claimed to be useful for treatment of osteoporosis and estrogen disorders. Amongst the voluminous literature in this field, M. Messina, Chemistry & Industry 1995, 413-415, and T. E. Wiese et al., ibid. 1997, 648-653, present interesting reviews on the biological effects and uses of isoflavones, including genistein.

The naturally occurring isoflavones formononetin and biochanin A, which in contrast to genistein and daidzein do not occur in soy, are of agricultural interest as promoters for mycorrhizal fungi which benefit plant growth.

Isoflavones are characterized by the following general berizopyranone structure, the ring numbering also being shown:

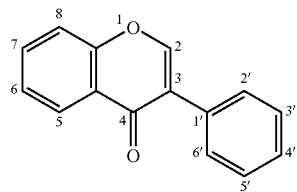

Many substances containing the isoflavone structure are found naturally, mainly in the family Leguminosiae; the richest sources are soy, lentils, chickpea, fenugreek, clover, alfalfa and various-types of beans. Genistein, for example, was first isolated in 1899 from broom (Genista tinctoria), and later, in 1931, isolated from Soya hispida [see A. G. Perkins et al., J. Chem. Soc. 75, 830 (1899), and E. Walz, Ann. Chem. 489, 118 (1931)]. Its structure was first determined by W. Baker and R. Robinson in 1926 (J. Chem. Soc. 1926, 2713), and the compound later synthesized (ibid. 1928, 3115).

Most frequently the isoflavones are substituted on the rings to varying degrees with hydroxy, alkoxy, prenyl and prenyl-derived groups, and the molecule may constitute part of a more complex ring structure. Naturally occurring isoflavones are often substituted at the hydroxy groups with sugars, which on their part are sometimes additionally substituted by ester groups. Isoflavone are commonly isolated in nature as mixtures with closely related substances. For example, isoflavones isolated from soybeans include genistein and daidzein which occur co-mixed as free aglycones (sugar-free forms) as well as their glycosides genistin and daidzin in soybeans to the extent of about 500-3000 ppm on a dry weight basis. Direct isolation from biomass containing such mixtures is thus complex and often largely economically impracticable.

It is known to experts in the pertinent technical field that other components in natural mixtures may alter the bioavailability and degree of bioactivity of the active isoflavone principles. In controlled studies, individual isoflavones from these mixtures also show differing biological activities, degrees of the desired activities, and side-effects. WO 93/23069, for example, discloses the differing activities of the isoflavones found in clover. Further recent studies suggest that isoflavone glycosides are less bioavailable than the free aglycones. Thus, isolation of isoflavone products from biomass ideally requires a hydrolytic step to cleave the glycosides and some type of reproducible fractionation operation to purify the isoflavones.

Soybeans are one of the few rich nutritional sources of natural isoflavones. As a high proportion of the isoflavones in soy occurs naturally as water-soluble glycosides, losses to aqueous sidestreams and wastes during protein manufacture occur to varying degrees depending on the manner of processing [Murphy, J. Agric. Food Chem. 44, 2377-2383 (1996)]. Some manufacturers of soy protein seek to retain the desirable isoflavones in soy food products by modifications of normal methods for soy protein production, for example as described in WO 00/17217, U.S. Pat. No. 6,140,469, and U.S. Pat. No. 5,994,508. Soy proteins can be treated with glycosidases to hydrolyze them, and the resulting aglycones then precipitate with the proteins as described in U.S. Pat. No. 5,320,949, U.S. Pat. No. 5,352,384, U.S. Pat. No. 5,632,561 and U.S. Pat. No. 5,637,562. Such methods provide food products with varying amounts of mixed isoflavones. However, apart from tofu and a few other forms of soy protein, human consumption of soy is not very prevalent in the Western World.

Isoflavone glycosides can be recovered from soy processing streams by various means. For example, U.S. Pat. No. 5,670,632 describes a process for the isolation of a concentrated mixture of isoflavone glycosides by ion-exchange adsorption/desorption. U.S. Pat. No. 5,679,806 describes a process for adsorption/desorption with polymeric resins of isoflavone glycosides from soy molasses or soy extracts. Under conditions of gradient elution chromatography, the glycosides maybe separated individually, isolated and purified. In U.S. Pat. No. 5,702,752 there is described a process of ultrafiltration for the recovery of mixed isoflavone glycosides. U.S. Pat. No. 6,033,714 describes a further process of ultrafiltration by which genistin, the glycoside of genistein, is selectively separated from soy molasses or soy whey. Each of these processes requires further purification of the glycoside and its hydrolysis to obtain the respective pure isoflavone.

Soy fractions are also used as part of the culture media for fermentations. As described in U.S. Pat. No. 5,554,519, genistein can be isolated as a by-product of the production of erythromycin. However, the production capacity is low and care must be taken to remove other fermentation products from the isoflavones in order to safely use them for human administration.

Unusually, a high concentration of isoflavones can be found in the biomass of plants of normal genetic origin. For example, clover contains genistein, daidzein, formononetin, biochanin and their glycosides in a total concentrations of 0.5 to 3.5% on a dry weight basis. Due to the higher content, isolation is more economically feasible. Thus, U.S. Pat. No. 6,146,668 describes solvent extraction of red clover in the presence of glycoside-hydrolyzing enzymes to obtain mixed isoflavones. These can then be further separated by extraction and crystallization to obtain individual isoflavones, such as genistein. The extraction generates large amounts of solvent-laden waste biomass. Furthermore, one consequence of the purification of genistein is the unavoidable co-production of significant amounts of daidzein which is of lesser value, as well as bioactive organic wastes.

The above examples serve to illustrate some of the disadvantages of isolating or otherwise obtaining isoflavones from higher abundance natural sources. Other useful or potentially useful isoflavones occur naturally in very low amounts and are thus not practical to isolate. Yet others are not directly available from natural sources but can be synthesized, albeit inefficiently and uneconomically. Thus there exists a need for practical procedures for efficiently manufacturing large amounts of pure isoflavones.

A number of chemical syntheses of isoflavones have been developed over many years, as reported in various reviews in the general and specialist literature of organic chemistry, such as The Chemistry of Flavonoid Compounds, Geissmann (ed.), Pergamon Press 1962; The Flavonoids, Harborne, Mabry and Mabry (eds), Academic Press 1975; The Flavonoids, Harborne (ed.), Chapman-Hall 1986; and Ellis, General Methods of Preparing Chromones, Chapter IX in Chromans, Chromenes and Chromanones, Wiley & Sons, 1972. The major synthetic procedures include rearrangement of flavanones and chalcones, condensations of phenols with beta-keto acids, esters or nitriles, coupling of substituents to preformed flavone rings, and acylations of 2-hydroxyaryl benzyl ketones ("2-hydroxydeoxybenzoins").

In the earlier years, from about 1928 to about 1952, two synthetic routes to genistein and related isoflavones were predominantly available. The first route involved the reaction of a 2-hydroxydeoxybenzoin with a cinnamic acid ester, e.g. ethyl cinnamate, to afford the corresponding 2-(2-phenylethenyl)-isoflavone, followed by oxidation with potassium permanganate and thermal decarboxylation to the isoflavanone compound: see W. Baker et al., J. Chem. Soc. 1926, 2713; ibid. 1928, 3115; and ibid. 1933, 274. The second route involved the reaction of a 2-hydroxydeoxybenzoin with sodium and ethyl formate to produce the appropriate 2H-isoflavone compound directly: see H. S. Mahal et al., J. Chem. Soc. 1934, 1769; F. Wessely et al., Chem. Ber. 66, 685 (1933); and R. L. Shriner, J. Org. Chem. 10, 288 (1945). Both routes in whatever variation led to inadequate yields of the desired isoflavone compound.

In later years, from about 1952, further methods were developed for synthesizing isoflavone compounds starting from appropriate 2-hydroxydeoxybenzoins [see A. Pelter et al., Synthesis 1978, 326 and 843, and Y.-C. Chang et al., J. Agric. Food Chem. 42, 1869 (1994)]. Three principle methods were employed for cyclizing the 2-hydroxydeoxybenzoin to the isoflavone compound: the first utilized formamide dimethylacetal and a large excess (at least eight equivalents) of the Lewis acid boron trifluoride etherate in dimethyl formamide [method (i)], the second involved the reaction of the 2-hydroxydeoxybenzoin with ethyl chlorooxalate in pyridine followed by saponification with ethanolic potassium hydroxide and thermal decarboxylation [method (ii)], and in the third method the 2-hydroxydeoxybenzoin was reacted with 1,3,5-triazine in the presence of boron trifluoride etherate and the mixture treated with acetic anhydride in acetic acid [method (iii)]: see specifically J. Chang et al., J. Agric. Food Chem. 42, 1869 (1994) and A. Pelter et al., Synthesis 1978, 843; W. Baker et al., J. Chem. Soc. 1953, 1852-1860; and H. C. Iha et al., Angew. Chem. 93, 129 (1981), respectively. The disadvantages of these three principle methods include the use of excess amounts of the corrosive and environmentally unacceptable boron trifluoride etherate or of amine waste products. Moreover, the method (ii) is complicated in involving essentially three reaction steps, and requires high temperatures for the decarboxylation. In all cases only moderate yields, at best, of the isoflavone compound were achieved.

Still further methods include:

(iv) reaction of an appropriate polyhydroxy substituted acetophenone, e.g. 2,4,6-trihydroxyacetophenone, of which some of the hydroxy groups are protected with hydroxy-protected p-hydroxybenzaldehyde, and subsequent oxidative cyclization with thallium (III) nitrate [L. Farkas et al., J. Chem. Soc. Perkin Trans. I, 305 (1974) and H. Sekizaki et al., Chem. Pharm. Bull. 36, 4876 (1988)];

(v) reaction of a 2-hydroxydeoxybenzoin with tert. butoxybis(dimethylamino)methane [K. C. Luk et al., J. Nat. Prod. 46, 852 (1983), P. F. Schuda et al., J. Org. Chem. 52, 1972-1979 (1987) and S. Sepulveda-Boza, Synth. Commun. 31, 1933-1940 (2001)];

(vi) reaction of a 2-hydroxydeoxybenzoin with zinc cyanide followed by cyclization with hydrochloric acid [L. Farkas, Chem. Ber. 90, 2940 (1957) and L. Farkas et al., ibid. 91, 2858 (1958)];

(vii) reaction of a 2-hydroxydeoxybenzoin with an activated dimethylformamide under various conditions [S. A. Kagal et al., Tetrahedron Lett. 1962, 593, A. C. Jain et al., Ind. J. Chem. 25B, 649-651 (1986), V. S. Parmav et al., Synth. Commun. 18, 511-517 (1988), R. J. Bass, J. Chem. Soc. Chem. Commun. 1976, 78, Y. C. Chang et al., J. Agric. Food Chem. 42, 1869 (1994), S. Sepulveda-Boza, Synth. Commun. 31, 1933-1940 (2001), K. Wähala et al., J. Chem. Soc. Perkin Trans. I, 1991, 3005 and K. Wähala et al., Proc. Soc. for Exper. Biol. and Med., 208, 27-32 (1995)]; and (viii) reaction of a 2-hydroxydeoxybenzoin with a trialkyl orthoformate under basic conditions [L. Parkas et al., J. Chem. Soc. Perkin Trans. I 1974, 305, U.S. Pat. No. 5,247,102, Japanese Patent Publication (Kokai) 09/157, 268 (1997) and A. Levai et al., Synth. Commun. 22, 1735-1750 (1992)].

A further approach pursued by various groups of chemists has involved the use of the mixed carboxylic acid anhydride formic-acetic anhydride as a reagent for reacting with a 2-hydroxydeoxybenzoin, with or without the presence of a base, to produce isoflavones such as genistein and biochanin A. Earlier investigations of this approach are reported by G. I. P. Becket et al. in Tetrahedron Lett. 1976, 719, and J. Chem. Res. Synop. 1978, 47, and by D. F. Liu et al. in J. Heterocyclic Chem. 28, 1641-1642 (1991). More recently, various groups around V. G. Pivovarenko have prepared many isoflavones, including those with either a hydroxy, a methoxy or a substituted phenyl group as the 3-substituent: see for example J. Heterocyclic Chem. USSR (Engl. translation) 5, 496-501 (1991) [translated from Khim. Get. Soed. 5, 625-631 (1991)], J. Heterocyclic Chem. USSR (Engl. translation) 5, 497-502 (1992) [translated from Khim. Get. Soed. 5, 595-600 (1992)] and Soviet Union (SU) Patent 1,333,674. In the reported syntheses Pivovarenko et al. used a large excess of the reagent acetic-formic anhydride, indeed as much as a 50 to 70 times excess; and likewise a large excess of base, e.g. about six equivalents. Such bases as sodium formate and tertiary amines, e.g. trimethylamine and tribenzylamine, have been employed. Furthermore, lengthy reaction times of up to 6 days appeared to have been necessary. Some reactions were effected in a solvent, others without.

It is known that acetic-formic anhydride decomposes noticeably at 0° C. into carbon monoxide and acetic acid, this decomposition becoming correspondingly more rapid as the temperature is raised. The reagent can be handled with appropriate safety precautions on the small scale, but becomes increasingly more difficult to handle safely on the large scale (see Giumini, Tetrahedron Lett. 1977, 3071, and P. Strazzolini et al., Tetrahedron 46, 1081-1118 (1990). As a further effect of the tendency of acetic-formic anhydride to decompose, the liberated acetic acid in the reactions of the anhydride with 2-hydroxydeoxybenzoins leads to the undesirable formation of the corresponding 2-methylisoflavones, which are difficult to separate from the 2H-isoflavones.

The conclusion from the above reported disadvantages of using acetic-formic anhydride in processes for producing isoflavones is that the reagent is unsuitable for use in such processes on the large, particularly commercial, scale.

Accordingly, there exists a need for a process for manufacturing 2H-isoflavones, e.g. genistein, which does not feature the aforementioned disadvantages, or at least avoids them to a significant extent. One approach amongst many others would be to replace the reagent acetic-formic anhydride with a reagent giving rise to the formyl moiety but which is selective in reacting with 2-hydroxydeoxybenzoins to afford a single product of high purity, i.e. in not giving rise to by-products in significant amounts. However, it cannot be predicted which reagents would be suitable sources of the formyl moiety, i.e. would meet these demands.

It has now been surprisingly found that anhydrides of formic acid and certain other carboxylic acids, apart from acetic acid, are suitable formylating agents for reacting with appropriate 2-hydroxydeoxybenzoins to produce 7-hydroxy- or 5,7-dihydroxy-2H-isoflavones.

The present invention provides a process for manufacturing a 7-hydroxy- or 5,7-dihydroxy-2H-isoflavone (hereinafter "hydroxylated isoflavone") of the general formula.

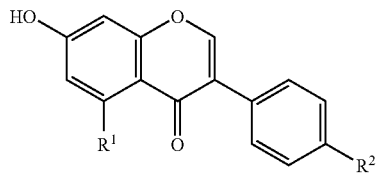

I wherein $R^1$ signifies hydrogen or hydroxy, and
$R^2$ signifies hydroxy or $C_{1-6}$-alkoxy, characterized by reacting a 2-hydroxydeoxybenzoin of the general formula

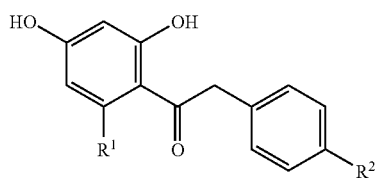

II wherein $R^1$ and $R^2$ have the significances given above, with a formic acid anhydride of the general formula

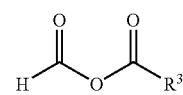

III wherein $R^3$ signifies $C_{2-20}$-alkyl, $C_{1-6}$-haloalkyl, ($C_{1-6}$-alkoxy)methyl, carboxy-$C_{2-6}$-alkyl, aryl-$C_{1-6}$-alkyl, a group —$CH_2$—$(OCH_2CH_2)_m$—O—$C_{1-6}$-alkyl, a group —$CH(R^4)$=$CR^5R^6$, a group —CH=CH—COOH, $C_{3-8}$-cycloalkyl, aryl, heteroaryl, di($C_{1-6}$-alkyl)aminomethyl, diarylaminomethyl, a group —$(CH_2)_n$—$COOR^7$, a group —$(CH_2)_m$—COOCHO, a group —CH=CH—COOCHO, $C_{1-6}$-alkoxy, aryloxy or formyloxy, each of $R^4$, $R^5$ and $R^6$, independently, signifies hydrogen) $C_{1-6}$-alkyl or aryl,
$R^7$ signifies hydrogen, $C_{1-6}$-alkyl or aryl,
m signifies an integer 1 to 4, and
n signifies zero or an integer 1 to 8, in the presence of a base or in a solvent which acts as a base, and if necessary promoting the ensuing hydrolysis of the so-produced acylated form of the hydroxylated isoflavone of the formula I by acidification.

The so-produced hydroxylated isoflavone of the formula I is according to the significances of $R^1$ and $R^2$ one of the following compounds:
genistein ($R^1$ and $R^2$ both signify hydroxy);
daidzein ($R^1$ and $R^2$ signify hydrogen and hydroxy, respectively);
biochanin A ($R^1$ and $R^2$ signify hydroxy and methoxy, respectively);
formononetin ($R^1$ and $R^2$ signify hydrogen and methoxy, respectively);
isoflavones of the formula I wherein $R^1$ signifies hydrogen or hydroxy and $R^2$ signifies $C_{2-6}$-alkoxy, i.e. an alkoxy group other than methoxy.

In the above definition of the symbols $R^2$, $R^3$, $R^4$, $R^5$, $R^6$ and $R^7$, and any references below to alkyl groups, any alkyl (from $C_3$) can be straight-chain or branched. This applies equally to "alkyl" (including any alkyl mentioned below in connection with the substitution of aryl or heteroaryl) as such or to the alkyl part of such groups as "$C_{1-6}$-haloalkyl", "($C_{1-6}$-alkoxy)methyl", "aryl-$C_{1-6}$-alkyl", "—$CH_2$—$(OCH_2CH_2)_m$—O—$C_{1-6}$-alkyl", "di($C_{1-6}$-alkyl)aminomethyl" and "$C_{1-6}$-alkoxy" (significances of $R^3$). An exception to this principle is the group "carboxy-$C_{2-6}$-alkyl", in which the alkyl moiety is always branched, as will be explained hereinafter.

Any halogen substituent, e.g. in "$C_{1-6}$-haloalkyl" or as a possible substituent for an aryl or heteroaryl group, is in each case fluorine, chlorine, bromine or iodine. In. "$C_{1-6}$-haloalkyl" itself there may-be one or more (same or different) halogen substituents, but the group preferably features a single halogen substituent.

In the group "di($C_{1-6}$-alkyl)aminomethyl" the two $C_{1-6}$-alkyl groups may be identical or different.

The expression "aryl", as such or as the aryl part of "aryl-$C_{1-6}$-alkyl", "diarylaminomethyl" or "aryloxy" (significances of $R^3$), means phenyl, 1-naphthyl or 2-naphythyl, or such a group featuring one or more substituents. Such substituents are particularly those selected from $C_{1-4}$-alkyl, $C_{1-4}$-alkoxy, halogen, nitro, cyano, di($C_{1-6}$-alkyl)amino, phenyl, carboxyl, ($C_{1-6}$-alkoxy)carbonyl and formyloxycarbonyl, whereby when two or more substituents are present these can be the same or different. Examples of substituted phenyl groups are p-tolyl, 3-methoxyphenyl, 4-methoxyphenyl, 2,5-dimethoxyphenyl, 3,4-dimethoxyphenyl, 2-carboxyphenyl and 2-(formyloxycarbonyl)-phenyl.

The expression "heteroaryl", also a significance of R³, means a 5- or 6-membered heterocyclic group of aromatic character featuring as ring member(s) one or more heteroatoms selected from oxygen, sulphur and nitrogen. Examples of such heteroaryl groups are 2- or 3-furyl, 2- or 3-thienyl and 4-pyridyl. As in the case of the aryl groups, the heteroaryl groups can be unsubstituted or substituted by one or more substituents as indicated hereinabove for the aryl groups featuring substituents.

On the face of it the groups carboxy-$C_{2-6}$-alkyl and —$(CH_2)_n$—COOR⁷, in the case where R⁷ in the latter group signifies hydrogen, may be considered to embrace members common to both. However, the former group is to be understood in the context of the present invention to exclude all those members of the latter group which contain 2 to 6 carbon atoms. Thus the $C_{2-6}$-alkyl moiety of "carboxy-$C_{2-6}$-alkyl" is always branched, and does not include methylene, dimethylene, trimethylene and the further polymethylenes embraced by —$(CH_2)_n$—.

The above formulae I, II and III embrace in each case isomeric forms, e.g. optically active or inactive and E/Z-isomers, as the case permits, as well as mixtures thereof, unless expressly stated to the contrary.

Of all the possibilities for the formic acid anhydride of the formula III, the preferred ones are propionic formic anhydride (R³ signifies ethyl), isobutyric formic anhydride (R³ signifies isopropyl), carbonic monoformic anhydride methyl ester (R³ signifies methoxy) and carbonic monoformic anhydride ethyl ester (R³ signifies ethoxy).

The process in accordance with the present invention is carried out by reacting the 2-hydroxydeoxybenzoin of the formula II with the formic acid anhydride the formula III under essentially basic conditions, i.e. in the presence of a base as the catalyst or in an organic solvent which acts as a base, whereby in the latter case no extra base needs to be included in the reaction medium. If a base is employed rather than an organic solvent which acts as a base, the process is preferably carried out additionally in an organic solvent. Moreover, the process is carried out at temperatures conveniently in the range of about −20° C. to about +80° C., preferably at temperatures from about −5° C. to about +45° C.

Suitable organic solvents are, in general, polar or slightly polar aprotic solvents. Such solvents are, for example, aliphatic and cyclic ethers, e.g. diethyl ether, diisopropyl ether, dibutyl ether, tert. butyl methyl ether, diethylene glycol dimethyl ether, tetrahydrofuran and dioxan; lower aliphatic nitriles, e.g. acetonitrile and propionitrile; lower aliphatic esters, e.g. lower alkyl formates and acetates; dimethylsulphoxide; halogenated, particularly chlorinated, lower aliphatic hydrocarbons, e.g. methylene chloride; aromatic hydrocarbons, e.g. benzene, toluene and xylenes; and lower aliphatic ketones, e.g. acetone, 2-butanone, diethyl ketone and methyl isobutyl ketone. Solvents which act as bases, and therefore which can be used without the presence of an added base in the reaction medium, include di(lower alkyl)formamides, e.g. dimethylformamide, dimethylacetamide, tetramethylurea and N-methyl-pyrrolidone. The preferred solvent is one which has a boiling point (at atmospheric pressure) of less than 80° C. and which is miscible with ethanol and preferably also with water. In these circumstances the employed such solvent can at the termination of the reaction be replaced with ethanol or aqueous ethanol, and the hydroxylated isoflavone product of the formula I can be isolated through crystallization induced by the addition of water (in general isoflavones are very sparingly soluble in water).

As the base for the reaction between the 2-hydroxydeoxybenzoin of the formula II and the formic acid anhydride of the formula III there is conveniently used an alkali metal or alkaline earth metal hydroxide, e.g. lithium, sodium or potassium hydroxide; an alkali metal or alkaline earth metal carbonate or bicarbonate, e.g. lithium, sodium or potassium carbonate, calcium or magnesium carbonate, lithium, sodium or potassium bicarbonate, or calcium or magnesium bicarbonate, as appropriate; an alkali metal or alkaline earth metal salt of a carboxylic acid with up to 10 carbon atoms, e.g. sodium formate or potassium propionate; an aliphatic or mixed aliphatic/aromatic tertiary amine, e.g. trimethylamine, triethylamine, N-ethyldiisopropylamine, N,N-dimethylethanolamine and esters thereof such as 2-(dimethylamino)-ethyl acetate, triethanolamine or N,N-dialkylaniline; a nitrogen-containing heterocyclic base, e.g. optionally alkyl substituted pyridine, a N-alkyl substituted piperidine, a N-alkyl substituted morpholine such as N-methyl-morpholine, or imidazole; or a secondary or tertiary phosphate, especially of an alkali metal, e.g. trisodium phosphate or tripotassium phosphate. The preferred type of base is an alkali metal or carbonate, bicarbonate or formate, or an aliphatic or mixed aliphatic/aromatic tertiary amine.

In general there are conveniently present in the reaction mixture about 1.5 to about 6 equivalents of the formic acid anhydride of the formula III per equivalent of the 2-hydroxydeoxybenzoin of the formula II, preferably about 2.5 to about 5 equivalents of the formic acid anhydride per equivalent of the 2-hydroxydeoxybenzoin. The base, when employed, is generally present in an amount which is up to about 6 equivalents per equivalent of the 2-hydroxydeoxybenzoin. The optimal amount depends very much on such factors as the nature of the base itself and of the employed solvent, and can be determined by appropriate investigation of the effects of reaction parameter variation on the ease of reaction and the purity and yield of the produced hydroxylated isoflavone.

Moreover, the reaction is conveniently effected at normal pressure, the pressure in general not being critical. Furthermore, the reaction mixture is suitably agitated, in particular stirred, to promote good admixture of the components and ensuing efficient reaction.

In general the course of the reaction can be observed by such conventional analytical techniques as HPLC, e.g. by monitoring the consumption of the starting 2-hydroxydeoxybenzoin.

In one particular procedure for the reaction the starting formic acid anhydride of the formula III is conveniently first produced by reacting sodium formate with the appropriate acid chloride of formula R³COCl, conveniently in a solvent which is usable for the subsequent (main) reaction of the formic acid anhydride with the 2-hydroxydeoxybenzoin, e.g. acetone. After completion of the reaction to produce the formic acid anhydride the appropriate amount of base is added, followed by the appropriate amount of the 2-hydroxydeoxybenzoin, after which the main reaction is effected as described above. As a variation of this procedure the base and the 2-hydroxydeoxybenzoin can both be added together to the freshly produced formic acid anhydride in the reaction solvent. After it has been established that most of the reaction to the desired, albeit in some cases acylated, product has been completed, a final reaction period, e.g. at somewhat elevated temperature, particularly in the range from about 40 to about 50° C., generally promotes the completion (cyclization). Otherwise, in situ methodology (one pot) can be employed.

After completion of the reaction of the formic acid anhydride of the formula III with the 2-hydroxydeoxybenzoin of the formula II the product can in principle be isolated. However, and as indicated above, the desired product has in many cases by this stage become acylated at its phenolic hydroxyl groups (7-OH, and the hydroxyl group(s) signified by $R^1$ and/or $R^2$). Accordingly, any such acylated hydroxyl groups must first be hydrolyzed to the free hydroxyl groups. The hydrolysis of the so-produced acylated form of the desired hydroxylated isoflavone is conveniently effected by addition of aqueous mineral acid, e.g. sulphuric acid or hydrochloric acid, and heating the acidified mixture. In the case of sulphuric acid its concentration is conveniently 5 to 50%, e.g. 10%. However, even concentrated sulphuric acid, e.g. sulphuric acid at a concentration approaching 100%, may be used if the reaction mixture is diluted with water prior tov the acid addition. If hydrochloric acid is used for the acidification to promote the hydrolysis, said acid is conveniently of a concentration of about 20%. The acidification drastically lowers the pH of the mixture to about 0-2, preferably about 0-1, and thus enables a more rapid hydrolysis to the desired hydroxylated isoflavone than would be achievable, albeit less practicably so, if the slightly acid (pH about 4-6) mixture were simply heated without additional acidification. Following the addition of acid the mixture is heated, optionally under increased pressure, to effect the hydrolysis. In a preferred procedure, the solvent is continually removed by distillation during the hydrolysis and continually replaced with a lower alkanol, such as methanol or ethanol, or with water to dilute the mixture; such solvent exchange is particularly practicable when a solvent with a lower boiling point than that of the added lower alkanol, e.g. acetone or tetrahydrofuran, has been employed previously as the reaction solvent. Otherwise), i.e. in those cases where a solvent of about the same or a higher boiling point than that of the lower alkanol has been used, as much as possible of said solvent is conveniently first distilled off, optionally under reduced pressure, and the lower alkanol added thereafter. In either case further acid may then be added to the mixture to restore the pH value to about 0-2, preferably about 0-1. After the solvent exchange, and optional additional acidification, the mixture is conveniently heated, preferably at reflux temperature, for a further period to complete the hydrolysis. In this case, too, it is convenient to observe the course of the hydrolysis (deacylation) by conventional analytical techniques such as HPLC in order to establish when the reaction has effectively been completed.

To isolate the desired product, directly from the mixture on completion of the reaction of the formic acid anhydride of the formula III with the 2-hydroxydeoxybenzoin of the formula II or following the subsequent acid-catalysed hydrolysis for deacylation, this is conveniently crystallized out by addition of water, suitably at elevated temperature, e.g. at about 50-60° C. The volume of added water is conveniently about a fifth to about a half of the volume of the mixture containing the product before water addition. Optionally after also cooling the aqueous crystalline medium, e.g. to a temperature from about room temperature to about 0° C., the crystalline product is removed, e.g. by filtration, and if desired can be washed, e.g. with a mixture of ethanol and water, or otherwise purified by conventional methods, for example employing an organic solvent in which the product is at the most sparingly soluble, and submitting the product to one or more recrystallizations. Especially suitable organic solvents for such purposes are ethanol, acetone, mixtures of both or mixtures of each with a relatively small proportion of water. The final step in such a purification procedure is usually a thorough drying of the product at elevated temperature and reduced pressure.

The starting 2-hydroxydeoxybenzoins of the formula II are known compounds, obtainable by known procedures. For example, to obtain the 2-hydroxydeoxybenzoin 1-(2,4,6-trihydroxyphenyl)-2-(4'-hydroxy)-ethanone, i.e. the compound of the formula II wherein $R^1$ and $R^2$ each signify hydroxy, phloroglucinol(1,3,5-trihydroxybenzene) is reacted with 4-hydroxyphenylacetonitrile in a Hoesch reaction [see Russ. Chem. Review. 31, 615-633 (1962)] to afford an intermediary, isolable iminium salt, which is then hydrolyzed to the desired product. References concerning this 2-hydroxydeoxybenzoin include W. Baker et al., J. Chem. Soc. 1926, 2713, and J. Chang et al., J. Agric. Food Chem. 42, 1869 (1994). The further 2-hydroxydeoxybenzoins of formula II can be produced analogously or are the subject of specific production processes described in the scientific literature.

The further starting materials, i.e. the formic acid anhydrides of the formula III, are in some cases known. In general, such starting materials can be produced for example by reacting sodium formate with the appropriate acid chloride of formula $R^3COCl$ in an organic solvent such as an aliphatic or cyclic ether, e.g. diethyl ether or tetrahydrofuran, respectively; or an aromatic hydrocarbon, e.g. toluene [see, for example P. Strazzolini et al., Tetrahedron 46, 1081-1118 (1990); R. Schijf et al., Rev. Trav. Chim. 85, 627 (1966); and L. I. Krimen, Org. Synth. 50, 1 (1970)]. A further known method for producing the formic acid anhydride starting materials of the formula III involves the reaction of formic acid with the appropriate acid anhydride of formula $(R^3CO)_2O$. Examples of such processes are published inter alia in R. Strazzolini et al. (as above); A. Béhal, Ann. Chim. 20, 411 (1900); W. Stevens et al., Rec. Trav. Chim. 83, 1287 (1964); and R. Schijf et al., Rec. Trav. Chim. 84, 594 (1965). A still further method, specifically for the production of those formic acid anhydrides of the formula III wherein $R^3$ signifies carboxy-$C_{2-6}$-alkyl, a group —CH=CH—COOH, phenyl substituted with carboxyl, phenyl substituted with formyloxycarbonyl, a group —$(CH_2)_m$—COOH, a group —$(CH_2)_m$—COOCHO or a group —CH=CH—COOCHO (all these groups being ones terminating with carboxyl or formyloxycarbonyl), involves the reaction of sodium formate with the appropriate di(acid chloride), examples of such di(acid chloride) starting materials being maleic acid dichloride, 1,2-dicarboxybenzene dichloride and succinic acid dichloride.

Some of the formic acid anhydrides of the formula III are known from the scientific literature, and these known examples, and some pertinent references in which they and (in most cases) their production are described, are as follows:

$R^3$=ethyl, n-propyl, isopropyl or tert. butyl: R. Schijf et al., Rev. Trans. Chim. 85, 627 (1966) and for ethyl and n-propyl, additionally R. Schijf et al., ibid. 84, 594 (1965); and E. J. Vlietstra et al., Recueil: J. of Royal Neth. Chem. Soc. 101, 460-462 (1982);

$R^3$=n-butyl: E. J. Vlietstra et al. (as above);

$R^3$=n-pentadecyl: Chem. Abs. 58469 (2001)

$R^3$=styryl: W. K. Fife et al., J. Org. Chem. 51, 3746-3748 (1986);

R³=phenyl and 4-methoxyphenyl: W. K. Fife et al., as above; and for phenyl additionally K. Kikukawa et al., J. Org. Chem. 46, 4413-4416 (1981) and G. F. Fanta, ibid. 29, 981 (1964);

R³=4-methylphenyl, 4-hexylphenyl and 4-phenylphenyl: W. K. Fife et al., U.S. Pat. No. 4,874,558; and for 4-methylphenyl additionally K. Kikukawa et al., as above;

R³=2-(methoxycarbonyl)-ethyl[—(CH$_2$)$_n$—COOR$^7$ wherein n is 2 and R$^7$ is methyl]: F. Cavalli et al., Int. J. Chem. Kinet. 33, 431-439 (2001);

R³=ethoxy: T. Pavasavan, J. Org. Chem. 29, 3422-3423 (1964);

R³=formyloxy: G. Frapper, J.A.C.S. 122, 5367-1570 (2000);

Those starting materials, i.e. formic acid anhydrides, of the formula III, which are not previously known can be produced by analogous methods to those for producing the known ones, i.e. analogous to the methods described above or which are indicated above by way of pertinent literature references.

The invention is illustrated by the following Examples.

EXAMPLE 1

The apparatus consisted of a 250 ml double-walled reactor fitted with a stirrer, a dropping funnel, a distillation column, argon gasification means, a thermometer and a thermostat.

To a stirred suspension of 10 g (0.145 mol) of sodium formate in 25 g of acetone at a temperature of 21-23° C. were added dropwise under an argon atmosphere 13 g (0.14 mol) of propionyl chloride. The mixture was stirred at 22-25° C. for 2 hours, then warmed to 35° C., stirred for a further hour and finally cooled to 20-23° C. Produced and present in the mixture was the desired starting material propionyl formic anhydride.

Thereafter, a solution of 9.2 g (0.035 mol) of 1-(2,4,6-trihydroxyphenyl)-2-(4'-hydroxyphenyl)-ethanone and 3.6 g (0.035 mol) of triethylamine in 60 g of acetone was added dropwise to the mixture containing propionyl formic anhydride, and the reaction mixture was stirred for 2 hours at 25° C. and for a further hour at 40° C., affording a beige-coloured suspension. To quench the reaction 10 g of ethanol were then added, the mixture was stirred for a further 30 minutes, and the resulting suspension was allowed to stand at room temperature for about 16 hours.

To promote the hydrolysis 5 g of 50% sulphuric acid were added dropwise to the suspension at room temperature. The mixture was heated to about 60° C. to remove about 101 g of distillate. Following the addition of 68 g of ethanol to replace the lost solvent a further 4 g of concentrated sulphuric acid were added dropwise, and the mixture was heated for a further 90 minutes at about 70° C. The distillate which had accumulated consisted principally of acetone and a minor proportion of ethanol.

Following the distillation, 186 g of water were added to the remaining mixture in the reactor within 30 minutes, and the resulting slurry was then cooled to 10° C., stirred for a further 60 minutes and then filtered. The collected solid material was washed twice with 30 ml of water to afford 10.7 g of a moist) beige-coloured solid. This was dried at 100° C./1 mbar (0.1 kPa) for 2 hours to yield 8.4 g of an off-white solid consisting of genistein, of 98.9% purity according to HPLC. The yield of genistein was calculated to be 88%.

6 g of the crude genistein product were dissolved in 180 g of ethanol at reflux temperature. Then 135 g of ethanol were distilled off under atmospheric pressure, and the resulting suspension was cooled to −20° C. and stirred for 1 hour at this temperature and subsequently filtered. The collected solid material was washed with 10 g of cold ethanol, and then dried for 2 hours at 100° C./1 mbar (0.1 kPa) to give 5 g of a white solid. The genistein had been produced in a purity of 99.7% (according to HPLC). The yield after this purification was 84%.

Analytical and spectral data of the product:
$^1$H-NMR (400MHz, d$_6$-DMSO): 13.0 (s, OH), 10.9 (s, OH), 9.6 (s, OH), 8.33 (s, C(2)-H), 7.37 (d, J=8 Hz, C(2')H and C(6')H), 6.81 (d, J=8 Hz, C(3')H and C(5')H), 6.38 (d, J~2 Hz, 1 H), 6.22 (d, J ~2 Hz, 1 H);
Mass spectroscopy: 270.2 (M$^+$, 100%);
Infrared (Nujol, cm$^{-1}$): 3411 (OH), 1654 (C═O);
Ultraviolet (ethanol): 261 nm (ε=73570, log ε=4.87);
Content acc. to HPLC: 99.7% (as given above);
M. Pt.: 303° C.

EXAMPLE 2

The apparatus was essentially the same as that described in Example 1, the reactor having a capacity of 500 ml, however.

46.3 g (0.5 mol) of propionyl chloride were added dropwise to a stirred suspension of 35.7 g (0.52 mol) of sodium formate and 26.3 g (0.1 mol) of 1-(2,4,6-trihydroxyphenyl)-2-(4'-hydroxyphenyl)-ethanone in 180 g of acetone at a temperature of 21-23° C. under an argon atmosphere. The mixture was stirred at 23-25° C. for 1 hour, and then heated for 1 hour at 35° C. To the suspension at 18-20° C. were added 10.1 g (0.1 mol) triethylamine. The reaction mixture was stirred at 21-22° C. for 2 hours and then heated 1 hour at 35° C. To quench the reaction 50 g of ethanol were then added and the mixture was stirred for a further 15 minutes.

To promote the hydrolysis 20 g of 50% sulphuric acid were added dropwise to the suspension, which was then heated to about 60° C. to remove 215 g of distillate. The lost solvent was replaced with 80 g of ethanol. Then a further 15 g of concentrated sulphuric acid were added dropwise, and the mixture heated for a further 90 minutes at about 70° C.

350 g of water were added to the mixture over 30 minutes. The resulting slurry was cooled, held 1 hour at 10° C., and filtered. The collected solid was washed twice with 40 g water and then with 40 g of 50% aqueous ethanol to afford 31 g of a moist beige-coloured product. This was then dried at 100° C./1 mbar (0.1 kPa) for 2 hours to afford 25.3 g of an off-white product, which according to HPLC analysis consisted of 98.4% by weight of genistein. The calculated yield of genistein was 92.2%.

20 g of the crude genistein product were suspended in 120 g of 35% aqueous ethanol, and the suspension was stirred at reflux temperature for 2 hours. The resulting slurry was cooled down to 0° C., stirred for 1 hour at that temperature and filtered. The collected solid was washed with 20 g of 35% aqueous ethanol and then dried at 100° C./1 mbar (0.1 kPa) for 2 hours to afford 19.5 g of an off-white product. HPLC analysis indicated that this consisted of 99% by weight of genistein. The yield of genistein after this further purification was 98%.

EXAMPLE 3

The apparatus was essentially the same as that described in Example 2.

55.5 g (0.6 mol) propionyl chloride were added dropwise at a temperature of 21-23° C. to a stirred suspension of 42.1 g (0.62 mol) of sodium formate in 90 g acetone under an argon atmosphere. The mixture was stirred at 25° C. for 2 hours, then heated for 1 hour at 35° C. A solution of 26.3 g (0.1 mol) of 1-(2,4,6-trihydroxyphenyl)-2-(4'-hydroxyphenyl)-ethanone and 20.4 g (0.2 mol) triethylamine in 165 g of acetone was added dropwise to the resulting suspension at 20-22° C. The reaction mixture was stirred at 21-22° C. for 2 hours. To quench the reaction 50 g of ethanol were then added and the mixture was stirred for a further 30 minutes.

To promote the hydrolysis 20 g of 37% aqueous hydrochloric acid were added dropwise and the mixture was allowed stand at room temperature for about 16 hours. The mixture was then heated to about 60° C. to remove 303 g of distillate. The lost solvent was replaced with 100 g of ethanol. Then 20 g of 37% aqueous hydrochloric acid were added dropwise, and the mixture heated for a further 90 minutes at about 70° C. 400 g of water were added to the resulting suspension at 75-80° C. over 30 minutes. The slurry was cooled, held 1 hour at 10° C., and then filtered. The solid was washed twice with 50 g water to afford 31.5 g of a moist beige-coloured product. This was then dried at 100° C./1 mbar (0.1 kPa) for 2 hours to afford 25.5 g of an off-white product. HPLC analysis indicated that this consisted of 98.3% by weight of genistein. The calculated yield of genistein was 93%.

20 g of the crude genistein product were dissolved in 600 g of ethanol at reflux temperature. Then 470 g of ethanol were distilled off under atmospheric pressure and 130 g of water were added dropwise at 75-80° C. The resulting suspension was cooled to 0° C. and stirred one hour at this temperature, then filtered. The filter cake was washed with 20 g of 50% aqueous ethanol, then dried at 100° C./1 mbar (0.1 kPa) for 2 hours to afford 19 g of a white product. HPLC analysis indicated that this consisted of 99.1% by weight of genistein. The yield of genistein after this further purification was 95.7%.

EXAMPLE 4

The apparatus was the same as that described in Example 1.

27.8 g (0.3 mol) of propionyl chloride were added dropwise to a suspension of 21.1 g (0.31 mol) of sodium formate and 13.1 g (0.05 mol) of 1-(2,4,6-trihydroxyphenyl)-2-(4'-hydroxyphenyl)-ethanone in 100 g of ethyl formate at a temperature of 23-26° C. under argon. The suspension was stirred for 2 hours at 25° C. and heated for 1 hour at 35° C. 10.2 g (0.1 mol) of triethylamine were added to the resulting mixture at an internal temperature of 18-22° C. The mixture was then stirred for 16 hours at room temperature. Then 20 g of ethanol were added and the suspension was stirred for 15 minutes.

Thereafter, to promote the hydrolysis, 20 g of 50% sulphuric acid were added dropwise and the mixture was heated to about 80° C. to remove 128 g of distillate. The lost solvent was replaced with 50 g of ethanol. 150 g of water were added over 30 minutes to the mixture. The resulting slurry was cooled, held 1 hour at 10° C., and then filtered. The solid was washed twice with 25 g water and then with 30 g of 50% aqueous ethanol to afford 13.6 g of a moist beige-coloured product. This was then dried at 100° C./1 mbar (0.1 kPa) for 2 hours to afford 12.7 g of a beige-coloured product. HPLC analysis indicated that this consisted of 98.7% by weight of genistein. The yield of genistein was 92.7%.

EXAMPLE 5

The apparatus was the same as that described in Example 1.

27.8 g (0.3 mol) of propionyl chloride were added dropwise to 21.1 g (0.31 mol) of sodium formate at a temperature of 23-25° C. under argon. The white suspension was stirred 2 hours at 25° C. and heated for 1 hour at 35° C. To this mixture were added 13.1 g (0.05 mol) of 1-(2,4,6-trihydroxyphenyl)-2-(4'-hydroxyphenyl)-ethanone and 10.2 g (0.1 mol) of triethylamine at an internal temperature of 20-22° C. The mixture was then stirred at 21-22° C. for 2 hours and heated for 2 hours at 35° C. 50 g of ethanol were added at 20° C. and the suspension was stirred for 15 minutes.

Thereafter, to promote the hydrolysis, 30 g of 50% sulphuric acid were added dropwise and the mixture was heated for 1 hour at 75° C. To the mixture were then added over 30 minutes 150 g of water. The resulting slurry was cooled, held for 1 hour at 10° C., and then filtered. The solid was washed twice with 20 g water then with 30 g of 50% aqueous ethanol to afford 13.6 g of a moist beige-coloured product. This was then dried at 100° C./1 mbar (0.1 kPa) for 2 hours to give 10.9 g of a beige-coloured product. HPLC analysis indicated that this consisted of 98.4% by weight of genistein. The yield of genistein was 79.5%.

EXAMPLE 6

The apparatus was the same as that described in Example 1.

A suspension of 21.1 g (0.31 mol) of sodium formate, 13.1 g (0.05 mol) of 1-(2,4,6-trihydroxyphenyl)-2-(4'-hydroxyphenyl)-ethanone and 6.9 g (0.05 mol) potassium carbonate in 100 g of acetone was stirred 1 hour at 25° C. under argon. To this mixture were added dropwise 27.8 g (0.3 mol) of propionyl chloride at a temperature of 21-23° C. The suspension was stirred for 16 hours at room temperature. Then 20 g of ethanol were added, and the suspension was stirred for 15 minutes.

Thereafter, to promote the hydrolysis, 20 g of 50% sulphuric acid were added dropwise and the mixture was heated to about 60° C. to remove the solvent. The lost solvent was replaced with 50 g of ethanol. Then a further 10 g of concentrated sulphuric acid were added dropwise, and the mixture heated for a further hour at about 80° C. To the mixture was added over 30 minutes 120 g of water. The slurry was cooled, held for 1 hour at 10° C. then filtered. The solid was washed twice with 20 g water and then with 30 g of 50% aqueous ethanol. This was then dried at 100° C./1 mbar (0.1 kPa) for 2 hours to give 9.3 g of a pale yellow product. HPLC analysis indicated that this consisted of 97.8% by weight of genistein. The yield of genistein was 67.5%.

EXAMPLE 7

The apparatus was the same as that described in Example 1.

27.8 g (0.3 mol) of propionyl chloride were added dropwise to a stirred suspension of 21.1 g (0.31 mol) of sodium formate and 13.1 g (0.05 mol) of 1-(2,4,6-trihydroxyphenyl)-2-(4'-hydroxyphenyl)-ethanone in 100 g of dimethylformamide at a temperature of 25-28° C. under an argon atmosphere. The mixture was stirred at 25° C. for 2 hours and then heated for 2 hours at 35° C. To quench the reaction 15 g of ethanol were then added and the mixture was stirred for a further 15 minutes.

To promote the hydrolysis, 20 g of 50% sulphuric acid were added dropwise to the suspension at room temperature, and the reaction mixture was distilled in vacuo at 80 mbar (8 kPa) and 70-80° C. to remove 75 g of solvent. Then a further 20 g of concentrated sulphuric acid were added dropwise, and the mixture was heated for a further hour at 80° C. To the mixture was added 150 g of water, which promoted crystallization. The resulting slurry was cooled, held for an hour at 10° C., and then filtered. The collected solid was washed twice with 25 g of water and once with 30 g of 50% aqueous ethanol. The solid was then dried at 10° C./1 mbar (0.1 kPa) for 2 hours to afford 10.5 g of an off-white product. HPLC analysis indicated that this consisted of 98.2% by weight of genistein. The yield of genistein was 77%.

EXAMPLE 8

The apparatus was the same as that described in Example 1.

11.8 g (0.255 mol) of formic acid were added dropwise under argon to 32.6 g (0.25 mol) of propionic acid anhydride at an internal temperature of 25° C. The mixture was stirred at 45° C. for 2 hours, then cooled to 20° C. A solution of 13.1 g (0.05 mol) of 1-(2,4,6-trihydroxyphenyl)-2-(4'-hydroxyphenyl)-ethanone in 70 g of acetone was then added at 20-22° C., followed by 5.1 g (0.05 mol) of triethylamine. The mixture was stirred at 22-23° C. for 2 hours. After the addition of a further 5.1 g of triethylamine, the mixture was stirred at room temperature for about 16 hours and then after warming at 40° C. for a further hour at this temperature. To quench the reaction, 25 g of ethanol were added and the mixture was stirred for 15 minutes.

Thereafter, to promote the hydrolysis, 10 g of 50% sulphuric acid were added dropwise and the mixture was heated to 60° C. to remove 85 g of distillate. The lost solvent was replaced with 50 g of ethanol. Then 10 g of concentrated sulphuric acid were added dropwise, and the mixture heated for a further 90 minutes at about 70° C. 180 g of water were added to the mixture over 30 minutes. The resulting slurry was cooled, held for 1 hour at 10° C., and then filtered. The solid was washed twice with 25 g of water then with 20 g of 50% aqueous ethanol to afford 14.2 g of a moist beige-coloured product. This was then dried at 100° C./1 mbar (0.1 kPa) for 2 hours to afford 11.3 g of an off-white product. HPLC analysis indicated that this consisted of 99% by weight of genistein. The yield of genistein was 86.5%.

EXAMPLE 9

The apparatus was the same as that described in Example 1.

11.8 g (0.255 mol) of formic acid were added dropwise under argon to 32.6 g (0.25 mol) of propionic acid anhydride and 13.1 g (0.05 mol) of 1-(2,4,6-trihydroxyphenyl)-2-(4'-hydroxyphenyl)-ethanone at an internal temperature of 25° C. The mixture was then stirred at 45° C. for 2 hours and cooled to 20° C. Then 5.1 g of triethylamine (0.05 mol) were added dropwise, and the mixture was stirred at 22° C. for 2 hours, after which a final 5.1 g of triethylamine were added and the mixture was stirred at room temperature for about 16 hours. The mixture was warmed to 40° C. and stirring continued for a further hour at this temperature. To quench the reaction, 25 g of ethanol were added and the mixture was stirred for 15 minutes.

Thereafter, to promote the hydrolysis, 10 g of 50% sulphuric acid were added dropwise and the mixture was heated for 1 hour at 75° C. Then 10 g of concentrated sulphuric acid and 35 g of ethanol were added dropwise, and the stirring continued for a further 90 minutes at this temperature. 180 g of water were added over 30 minutes to the mixture. The resulting slurry was cooled, held for 1 hour at 10° C., and then filtered. The solid was washed twice with 25 g of water then with 20 g of 50% aqueous ethanol to afford 13.6 g of a moist beige-coloured product. This was then dried at 100° C./1 mbar (0.1 kPa) for 2 hours to afford 11.3 g of an off-white product. HPLC analysis indicated that this consisted of 98.5% by weight of genistein. The yield of genistein was 82.5%.

EXAMPLE 10

The apparatus was essentially the same as that described in Example 1.

42.1 g (0.3 mol) benzoyl chloride were added dropwise under an argon atmosphere to a stirred suspension of 21.1 g (0.31 mol) of sodium formate in 45 g of acetone at a temperature of 21-23° C. The mixture was stirred at 25° C. for 2 hours, then heated for 1 hour at 40° C. To the resulting suspension at 20-22° C. was added dropwise a solution of 13.1 g (0.05 mol) 1-(2,4,6-trihydroxyphenyl)-2-(4'-hydroxyphenyl)-ethanone and 10.2 g (0.1 mol) triethylamine in 75 g of acetone. The reaction mixture was stirred at 21-22° C. for 2 hours, then heated for 1 hour at 35° C. Then 20 g of ethanol were added, and the mixture was stirred for 15 minutes.

To promote the hydrolysis 20 g of 50% aqueous sulphuric acid were added dropwise and the mixture was allowed stand at room temperature for about 16 hours. The mixture was then heated to about 60° C. to remove the solvent. The lost solvent was replaced with 50 g of ethanol. Then 15 g of concentrated sulphuric acid were added dropwise, and the mixture was heated for a further 3.5 hours at about 70° C. 100 g of water were added to the resulting suspension at 75-80° C. over 30 minutes. The mixture was cooled at 20° C. and extracted four times with 100 ml of ethyl acetate. The organic layer was then heated to 40° C./150 mbar (15 kPa) to remove about 300 ml of distillate. The slurry was cooled, allowed stand at room temperature for about 16 hours and filtered. The solid was washed with 10 ml of ethyl acetate to afford 11.5 g of a moist beige-coloured product.

The crude genistein product was suspended in 60 g of 50% aqueous ethanol, and the suspension was stirred at reflux temperature for 1 hour. The resulting suspension was cooled to 5° C. and stirred for one hour at this temperature, then filtered. The filter cake was washed with 10 g of 50% aqueous ethanol, then dried at 100° C./1 mbar (0.1 kPa) for 2 hours to afford 7.3 g of an off-white product. HPLC analysis indicated that this consisted of 97.5% by weight of genistein. The yield of genistein after this further purification was 52.7%. 1

EXAMPLE 11

The apparatus was the same as that described in Example 2.

55.4 g (0.5 mol) of ethyl chloroformate were added dropwise under argon to a suspension of 35.7 g (0.51 mol) of sodium formate and 26.3 g (0.1 mol) of 1-(2,4,6-trihydroxyphenyl)-2-(4'-hydroxyphenyl)-ethanone in 150 g of acetone at a temperature of 0-5° C. The suspension was stirred for 3 hours at 0-5° C. To the resulting mixture were added dropwise 15.2 g (0.15 mol) of triethylamine at an internal temperature of 0-5° C. The mixture was then stirred for 1 hour at 0-5° C. and for 16 hours at room temperature.

The mixture was heated to about 60° C. to remove 160 g of distillate. The lost solvent was replaced with 80 g of ethanol. Thereafter, 50 g of 50% sulphuric acid were added over 15 minutes and the mixture was heated for 3 hours at about 70° C. To the mixture were added over 30 minutes 350 g of water. The resulting slurry was cooled, held for 1 hour at 30° C., and then filtered. The solid was washed twice with 40 g of water and once with 50 g of 50% aqueous ethanol to afford 32.1 g of a moist beige-coloured product. This was then dried at 100° C./1 mbar (0.1 kPa) for 2 hours to afford 26.3 g of a beige-coloured product. HPLC analysis indicated that this consisted of 81.1% by weight of genistein.

1 g of the crude genistein product were dissolved in 25 g of ethanol at reflux temperature. Then 5 g of 50% sulphuric acid were added dropwise and the mixture heated for a further 2 hours to about 100° C. under a pressure of 2 bar (0.2 MPa). Then 15 g of ethanol were distilled off under atmospheric pressure, and 5 g of water were added dropwise at 75-80° C. The resulting suspension was cooled to 20° C. and stirred 2 hours at this temperature, then filtered. The collected solid was dried at 100° C./1 mbar (0.1 kPa). for 2 hours to afford 0.9 g of an off-white product. HPLC analysis indicated that this consisted of 98.5% by weight of genistein.

EXAMPLE 12

The apparatus was the same as that described in Example 2.

60 g (0.65 mol) of propionyl chloride were added dropwise to a stirred suspension of 51 g (0.75 mol) of powdered sodium formate and 26.3 g (0.1 mol) of 1-(2,4,6-trihydroxyphenyl)-2-(4'-hydroxyphenyl)-ethanone in 200 g of acetone at a temperature of 21-23° C. The suspension was stirred at 23-25° C. for 30 minutes then heated for 13 hours at 32° C.

Thereafter, to promote the hydrolysis, 50 g of 50% sulphuric acid were added dropwise at 10-12° C. and the mixture was heated to about 60° C. to remove 204 g of distillate. The lost solvent was replaced with 120 g of ethanol. Then a further 25 g of 50% sulphuric acid were added dropwise, and the mixture heated for a further 1 hour at about 72° C. To the mixture was added over 30 minutes 300 g of water. The slurry was cooled, held for 1 hour at 30° C. and then filtered. The solid was washed twice with 40 g of water and once with 50 g of 50% aqueous ethanol. This was then dried at 100° C./1 mbar (0.1 kPa) for 2 hours to afford 21.6 g of a white product. HPLC analysis indicated that this consisted of 99.3% by weight of genistein. The yield of genistein was 79.4%.

EXAMPLE 13

The apparatus was the same as that described in Example 2.

54.4 g (0.5 mol) of isobutyryl chloride were added dropwise under argon to a suspension of 35.7 g (0.51 mol) of sodium formate and 26.3 g (0.1 mol) of1-(2,4,6-trihydroxyphenyl)-2-(4'-hydroxyphenyl)-ethanone in 150 g of acetone at a temperature of 21-23° C. The suspension was stirred for 1 hour at 23-25° C. and heated for 2 hours at 30-32° C. To the resulting mixture were added 15.2 g (0.15 mol) of triethylamine at an internal temperature of 18-22° C. The mixture was then stirred for 1 hour at 21-22° C. and heated at 30-32° C. for 1 hour.

Thereafter, to promote the hydrolysis, 50 g of 50% sulphuric acid were added dropwise and the mixture was heated to about 60° C. to remove 148 g of distillate. The lost solvent was replaced with 120 g of ethanol. The mixture was heated for a further 3 hours at about 70° C. To the suspension were added over 30 minutes 350 g of water. The resulting slurry was cooled, held for 1 hour at 30° C., and then filtered. The solid was washed twice with 40 g water and once with 50 g of 50% aqueous ethanol to afford 31.6 g of a moist off-white product. This was then dried at 100° C./1 mbar (0.1 kPa) for 2 hours to afford 24.5 g of an off-white product. HPLC analysis indicated that this consisted of 99.6% by weight of genistein. The yield of genistein was 90.3%.

The invention claimed is:

1. A process for manufacturing a hydroxylated isoflavone of the general formula

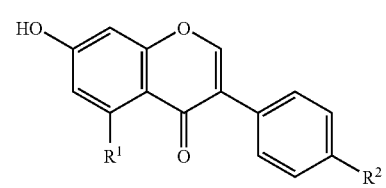

I wherein $R^1$ signifies hydrogen or hydroxy, and
$R^2$ signifies hydroxy or $C_{1-6}$-alkoxy,
comprising reacting a 2-hydroxydeoxybenzoin of the general formula

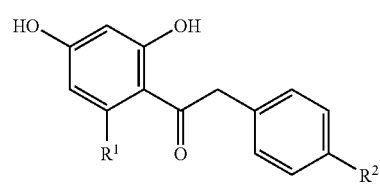

II wherein $R^1$ and $R^2$ are defined as above, with a formic acid anhydride of the general formula

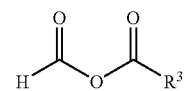

III wherein $R^3$ signifies $C_{2-20}$-alkyl, $C_{1-6}$-haloalkyl, ($C_{1-6}$-alkoxy)methyl, carboxy-$C_{2-6}$-alkyl, aryl-$C_{1-6}$-alkyl, a group —$CH_2$—$(OCH_2CH_2)_m$—O—$C_{1-6}$-alkyl, a group —$CH(R^4)$=$CR^5R^6$, a group —CH=CH—COOH, $C_{3-8}$-cycloalkyl, aryl, heteroaryl, di($C_{1-6}$-alkyl)aminomethyl, diarylaminomethyl, a group —$(CH_2)_n$—$COOR^7$, a group —$(CH_2)_m$—COOCHO, a group —CH=CH—COOCHO, $C_{1-6}$-alkoxy, aryloxy or formyloxy,
each of $R^4$, $R^5$ and $R^6$, independently, signifies hydrogen, $C_{1-6}$-alkyl or aryl,
$R^7$ signifies hydrogen, $C_{1-6}$-alkyl or aryl,
m signifies an integer 1 to 4, and
n signifies zero or an integer 1 to 8,
in the presence of a base or in a solvent which acts as a base, and if necessary promoting the ensuing hydrolysis of the so-produced acylated form of the hydroxylated isoflavone of the formula I by acidification.

2. The process according to claim 1, wherein a base is employed and the process is carried out additionally in an organic solvent.

3. The process according to claim 2, wherein the base is an alkali metal or alkaline earth metal hydroxide, an alkali metal or alkaline earth metal carbonate or bicarbonate, an alkali metal or alkaline earth metal salt of a carboxylic acid with up to 10 carbon atoms, an aliphatic or mixed aliphatic/aromatic tertiary amine, a nitrogen-containing heterocyclic base, or a secondary or tertiary phosphate.

4. The process according to claim 3, wherein the base is lithium, sodium or potassium hydroxide, lithium, sodium or potassium carbonate, calcium or magnesium carbonate, lithium, sodium or potassium bicarbonate, calcium or magnesium bicarbonate, sodium formate, potassium propionate, trimethylamine, triethylamine, N-ethyldiisopropylamine, N,N-dimethylethanolamine, 2-(dimethylamino)-ethyl acetate, triethanolamine, N,N-dialkylaniline, optionally alkyl substituted pyridine, a N-alkyl substituted piperidine, a N-alkyl substituted morpholine, imidazole, trisodium phosphate or tripotassium phosphate.

5. The process according to claim 3, wherein the base is an alkali metal carbonate, bicarbonate or formate, or an aliphatic or mixed aliphatic/aromatic tertiary amine.

6. The process according to claim 2, wherein the solvent is an aliphatic or cyclic ether, a lower aliphatic nitrile, a lower aliphatic ester, dimethyl-sulphoxide, a halogenated, particularly chlorinated, lower aliphatic hydrocarbon, an aromatic hydrocarbon or a lower aliphatic ketone.

7. The process according to claim 6, wherein the solvent is diethyl ether, diisopropyl ether, dibutyl ether, tert. butyl methyl ether, diethylene glycol dimethyl ether, tetrahydrofuran, dioxan, acetonitrile, a lower alkyl formate or acetate, dimethylsulphoxide, methylene chloride, benzene, toluene, an xylene, acetone, 2-butanone, diethyl ketone or methyl isobutyl ketone.

8. The process according to claim 1, wherein the process is carried out in a solvent which acts as a base, and said solvent is a di(lower alkyl)formamide, preferably dimethylformamide, dimethylacetamide, tetramethylurea or N-methyl-pyrrolidone.

9. The process according to claim 1, wherein the process is carried out at temperatures in the range of about −20° C. to about +80° C., preferably at temperatures from about −5° C. to about +45° C.

10. The process according to claim 1, wherein about 1.5 to about 6 equivalents, preferably about 2.5 to about 5 equivalents, of the formic acid anhydride of the formula III are present in the reaction mixture per equivalent of the 2-hydroxydeoxy-benzoin of the formula II.

11. The process according to claim 2, wherein the base is present in the reaction mixture in an amount which is up to about 6 equivalents per equivalent of the 2-hydroxydeoxy-benzoin of the formula II.

12. The process according to claim 1, wherein the hydrolysis of any produced acylated form of the desired hydroxylated isoflavone of the formula I in the mixture after reaction is effected by addition of aqueous mineral acid to lower the pH of the mixture to about 0-2, preferably about 0-1, and heating the acidified mixture.

13. The process according to claim 12, wherein the solvent is continually removed by distillation during the hydrolysis and continually replaced with a lower alkanol, preferably methanol or ethanol, or with water to dilute the mixture, or wherein as much as possible of the solvent is first distilled off, optionally under reduced pressure, and the lower alkanol or water added thereafter, and in either case further acid is then optionally added to the mixture to restore the pH value to about 1-2, preferably about 0-1, and the mixture is heated, preferably at reflux temperature, for a further period to complete the hydrolysis.

14. The process according to claim 1, wherein the desired product of the formula I is isolated, either directly from the mixture on completion of the reaction of the formic acid anhydride of the formula III with the 2-hydroxydeoxybenzoin of the formula II or following the subsequent acid-catalysed hydrolysis for deacylation, by crystallization induced by addition of water and removal of the resulting crystalline product by filtration.

15. The process according to claim 1, wherein propionic formic anhydride is used as the formic acid anhydride of the formula III.

16. The process according to claim 1, wherein isobutyric formic anhydride, carbonic monoformic anhydride methyl ester or carbonic monoformic anhydride ethyl ester is used as the formic acid anhydride of the formula III.

* * * * *